United States Patent [19]

Tachibana et al.

[11] Patent Number: 5,281,527
[45] Date of Patent: Jan. 25, 1994

[54] PROCESS FOR PRODUCING PULLALANASE

[75] Inventors: Yoshihisa Tachibana; Iwao Kojima; Ritsuko Yoshida; Tomoko Adachi; Yoshiaki Takesada; Saburo Yamauchi, all of Fukuchiyama, Japan

[73] Assignee: Nagase Biochemicals, Ltd., Osaka, Japan

[21] Appl. No.: 902,739

[22] Filed: Jun. 23, 1992

[30] Foreign Application Priority Data

Jul. 5, 1991 [JP] Japan .................................. 3-192491

[51] Int. Cl.$^5$ ............................................. C12N 9/44
[52] U.S. Cl. ...................................... 435/210; 435/95; 435/98
[58] Field of Search .................. 435/95, 98, 210, 102, 435/801, 822

[56] References Cited

U.S. PATENT DOCUMENTS 4,628,028 12/1986 Katkocin et al. ...................... 435/95
5,055,403 10/1991 Tomimura .......................... 435/210

OTHER PUBLICATIONS

*Agric. Biol. Chem.*, 52 (9), 1988, pp. 2293–3398, Kusano et al., "Purification and Properties of *Bacillus acidopulluylticus* Pullalanase".

Souta et al., *Chemical Abstracts*, vol. 111 (9), 1989, #73578q.

*Primary Examiner*—Johnnie R. Brown
*Assistant Examiner*—Pamela S. Webber
*Attorney, Agent, or Firm*—Armstrong, Westerman, Hattori, McLeland & Naughton

[57] ABSTRACT

This invention provides a pullulanase having a high degree of pH stability under acidic conditions, which is produced by cultivation of a microorganism belonging to the genus Bacillus, particularly *Bacillus circulans* SV-98 (FERM P-12161). This enzyme is useful, for example, in the manufacture of glucose and maltose from starch.

1 Claim, No Drawings

PROCESS FOR PRODUCING PULLALANASE

This invention relates to a novel pullulanase and to a process for producing the same. More particularly, it relates to a novel pullulanase obtained by cultivation of a microorganism belonging to the genus Bacillus, and to a process for producing the same.

PRIOR ART

α-1,6-Glucosidases, such as pullulanase and isoamylase, are known to be effective in increasing the yield of sugars when used, in combination with glucoamylase, for the manufacture of glucose from starch and when used, in combination with β-amylase, for the manufacture of maltose from starch. As examples of the α-1,6-glucosidase heretofore reported may be mentioned isoamylase produced by *Escherichia intermedia* [Applied Microbiol, 15, 492 (1967)]; pullulanase produced by *Streptococcus mitis* [Biochem. J., 108, 33 (1968)], isoamylase produced by Streptomyces sp. [J. Ferment. Tech., 49, 552 (1971) ], and pullulanase produced by Bacillus sp. [Agric. Biol. Chem., 40. 1515 (1976); Starch, 34, 340 (1982)]. However, these α-1,6-glucosidases are low in thermal stability and pH stability, and the optimum temperature is about 40° to 50° C. in most cases.

PROBLEMS TO BE SOLVED BY THE INVENTION

Starch sugars are generally manufactured at a temperature as high as 60° C. or higher and under acidic conditions at a pH value of 4.5 or lower. As the pullulanase which acts under such conditions, are known only those produced by *Bacillus acidpullulyticus* (Japanese Patent Publication No.25037/1987) and *Bacillus sectorramus* (Japanese Patent Kokai No.84485/1988). However; the pH value of 4.5 or lower is close to the limit of the stable pH range for these two enzymes, and hence there has been a demand for α-1,6-glucosidases having a high degree of pH stability under more acidic conditions.

MEANS TO SOLVE THE PROBLEMS

The present inventors searched for a microorganism producing a thermostable α-1,6-glucosidase having the optimum pH and the stable pH range on the acidic side extensively in the natural world and discovered that *Bacillus circulans* SV-98 isolated from the soil in Fukuchiyama City in Kyoto Prefecture, Japan is the one that achieves the above object. This invention was accomplished on the basis of these findings.

Thus, the novel pullulanase of this invention has the physicochemical properties as listed below.

(a) Effects and substrate specificity

It acts on pullulan to form mainly maltotriose, and decomposes the α-1,6-glucoside linkages in amylopectin, β-limit dextrin and soluble starch.

(b) Optimum pH and pH stability

Its optimum pH is close to 5.0, and it remains stable in the pH range between 3.0 and 6.5 when heated at 50° C. for 30 minutes.

(c) Thermal stability

It remains stable at temperatures up to 55° C. when held for 30 minutes at pH 5.0.

(d) Optimum temperature

The optimum temperature is in the range between 55° and 60° C.

(e) Molecular weight

The molecular weight measured by electrophoresis on sodium dodecyl sulfate is 98000.

(f) Isoelectric point

The isoelectric point measured by isoelectric focusing is 4.7.

The novel pullulanase of this invention is produced by a microorganism belonging to the genus Bacillus, particularly *Bacillus circulans* SV-98 (FERM P-12161 now FERM BP-3896, on deposit at the Fermentation Research Institute, Agency of Industrial Science and technology, Ibaraki-ken, Japan). This strain has the physiological properties as listed below. The test of its physiological properties and its identification were performed according to the methods described in "Bergey's Mannual of Determinative Bacteriology (8th edition, 1974)" and in "Bergey's Mannual of Systematic Bacteriology (Vol. 2, 1986)".

| A. Form | | |
|---|---|---|
| (1) | Cell shape | Rods |
| (2) | Cell size | $0.4 \sim 0.5 \times 3.0 \sim 8.0 \, \mu m$ |
| (3) | Mobility | Positive |
| (4) | Spores | Present |
| (5) | Gram stain | Positive |
| (6) | Acid-fast stain | Negative |
| B. Growth in various media | | |
| (1) | Standard agar plate culture | Colony is circular; surface is slightly rough and white. |
| (2) | Standard agar slant culture | Surface is slightly rough and white. |
| (3) | Standard liquid culture | Slightly turbid with precipitate; No pigments. |
| (4) | Standard gelatin stab culture | No change |
| (5) | Litmus milk | No change |
| C. Physiological properties | | |
| (1) | Reduction of nitrates | Positive |
| (2) | Denitrification | Negative |
| (3) | Methyl red test | Negative |
| (4) | Voges-Proskauer test | Negative |
| (5) | Formation of indole | Negative |
| (6) | Formation of hydrogen sulfide | Negative |
| (7) | Hydrolysis of starch | Positive |
| (8) | Utilization of citrates | Negative |
| (9) | Utilization of inorganic nitrogen sources | |
| | Nitrates | Positive |
| | Sodium salts | Negative |
| (10) | Formation of pigments | Forms insoluble yellow pigment on sugar-ammonium agar plate culture. |
| (11) | Urease activity | Negative |
| (12) | Oxidase activity | Positive |
| (13) | Catalase activity | Positive |
| (14) | Growth temperature range | 15~45° C. |
| (15) | Response to oxygen gas | Facultative anaerobic |
| (16) | Formation of dihydroxyacetone | Negative |
| (17) | Hydrolysis of hippuric acid | Negative |
| (18) | Hydrolysis of arginine | Negative |
| (19) | Deamination of phenylalanine | Negative |
| (20) | Growth after thermal treatment (85° C., 10 minutes) | Positive |
| (21) | Growth in 2% NaCl | Negative |
| (22) | Growth in Sabouraud agar culture | Positive |

-continued

| | | |
|---|---|---|
| (23) | Growth with 0.001% lysozyme | Positive |
| (24) | Degradation of tyrosine | Positive |
| (25) | Alkaline in citrate.ammonium agar culture | Negative |
| (26) | Hydrolysis of casein | Negative |
| (27) | Hydrolysis of gelatine | Negative |
| (28) | Growth in anaerobic agar culture | Positive |
| (29) | Growth in MacConkey culture | Negative |
| (30) | Egg-yolk lecithinase activity | Negative |
| (31) | Alkaline in Voges-Proskauer broth | Negative |
| (32) | Acid formation from sugars | |
| | (a) L-Arabinose | Positive |
| | (b) D-Xylose | Positive |
| | (c) D-Glucose | Positive |
| | (d) D-Mannose | Positive |
| | (e) D-Fructose | Positive |
| | (f) D-Galactose | Negative |
| | (g) Maltose | Negative |
| | (h) Sucrose | Positive |
| | (i) Lactose | Negative |
| | (j) Trehalose | Positive |
| | (k) D-Sorbitol | Positive |
| | (l) D-Mannitol | Negative |
| | (m) Inositol | Negative |
| | (n) Glycerol | Negative |
| | (o) Starch | Negative |
| | (p) Melibiose | Positive |
| | (q) Salicin | Negative |
| | (r) Ethanol | Negative |

As a pullulanase produced by *Bacillus circulans*, has been reported the one produced by *Bacillus circulans* F-2 strain (Japanese Patent Kokai No.60376/1989). However, its molecular weight measured by electrophoresis on sodium dodecyl sulfate is 218000, and it also has amylase activity other than pullulanase activity. Table 1 shows its physicochemical properties concerning pullulanase activity compared with those of the pullulanase of this invention.

TABLE 1

Comparison of pullulanase produced by *Bacillus circulans* F-2 and pullulanase of this invention

| | Bacillus circulans F-2 strain | Enzyme of this invention |
|---|---|---|
| Optimum pH | pH 7.0 | pH 5.0 |
| pH Stability | pH 5.0~8.0 | pH 3.0~6.5 |
| Optimum temperature | 50° C. | 55~60° C. |
| Thermal stability | 40° C. or lower | 55° C. or lower |
| Molecular weight | 218000 | 98000 |

As is apparent from the above table, the pullulanase of this invention is clearly different from the amylase produced by *Bacillus circulans* F-2 strain and having pullulanase activity in physicochemical properties, and this indicates that the pullulanase of this invention and *Bacillus circulans* SV-98 which is the strain producing the same are both novel ones.

Production of the pullulanase of this invention by this microorganism may be performed continuously or intermittently by stationary culture, by shake culture, by culture with a jar fermentor or by solid culture. The culture medium used may contain, as required, a nitrogen source, such as an organic nitrogen source (e.g., polypeptone, yeast extract, meat extract, soybean powder, corn steep liquor and corn meal) and an inorganic nitrogen source (e.g., ammonium sulfate, ammonium chloride, ammonium nitrate and ammonium phosphate); and a carbon source, such as millet jelly, maltose, a variety of starch, soluble starch, liquefied starch, dextrin and pullulan. The medium may also contain, as required, phosphoric acid, various vitamins, and a salt, such as $Mg^{2+}$, $Ca^{2+}$, $Mn^{2+}$, $Fe^{2+}$, $Fe^{3+}$, $Zn^{2+}$, $Co^{2+}$, $Na^+$ and $K^+$. The proper pH of the culture medium is in the range from 4.0 to 8.0, preferably in the range from 5.0 to 6.0, and cultivation should preferably be carried out at a temperature in the range from 20° to 45° C., preferably in the range from 37° to 42° C. Cultivation is continued for a period of time sufficient for the growth of said microorganism and for the production of pullulanase, usually for a time in the range from 6 to 48 hours.

The cultured broth is then centrifuged or filtered to remove the microbial cells, and the supernatant or the filtrate thus obtained is subjected to salting-out or to solvent precipitation (by the use of ethanol, acetone, etc.) to precipitate the protein, or concentrated by ultrafiltration, thus isolating the pullulanase of this invention. When the method of salting-out or solvent precipitation is used, the precipitated pullulanase collected by filtration or centrifugation is subjected to desalting treatment, followed by freeze-drying, thus giving dry powder. The product thus obtained can be refined into an enzyme with enhanced specific activity by a suitable combination of ordinary purifying operations, such as salting-out, solvent precipitation, isoelectric precipitation, electrophoresis, ion-exchange chromatography, gel filtration, affinity chromatography and crystallization.

The pullulanase activity is measured and defined as described below. A mixture of 2% (w/v) solution of pullulan in 0.2M acetate buffer of pH 4.5 (0.5 ml) and an enzyme solution (0.5 ml) is incubated at 60° c. for 30 minutes, and the concentration of the liberated reducing ends is measured by the DNS method [Laboratory Experiments in Biological Chemistry, 3435, (1944)]. The amount of enzyme which forms reducing sugar corresponding to 1 $\mu$mol glucose as standard per 1 minute under the assay conditions described above is defined as "One unit".

The following Examples will further illustrate the invention, but are not intended to limit its scope.

EXAMPLE 1

*Bacillus circulans* SV-98 (FERM P-12161 was inoculated onto 10 ml of a medium containing 1.0% pullulan, 0.5% polypeptone, 0.5% yeast extract, 0.5% NaCl, 0.05% $MgSO_4.7H_2O$, 0.001% $MnCl_2$, 0.05% $CaCl_2.2H_2O$, 0.2% $KH_2PO_4$ and 0.2% $(NH_4)_2SO_4$ (pH 6.0 ), and cultivation was aerobically carried out at 37° C. for 16 hours by the shake culture method. The cultured solution thus obtained was subjected to centrifugation (10000 rpm, 10 minutes) to remove the microbial cells and other insoluble matters, the supernatant was collected, and its pullulanase activity (as an enzyme solution) was measured. The measured activity was 5.3 unit/ml.

EXAMPLE 2

The seed culture (10 ml) obtained by cultivation of *Bacillus circulans* SV-98 at 37° C. for 16 hours by using the culture medium and the culture method described in Example 1 was added to five liters of a culture medium (pH 6.0) placed in a 10-liter jar fermentor (containing 2.0% pullulan, 1.0% polypeptone, 1.0% yeast extract, 0.5% NaCl, 0.05% MgSO$_4$.7H$_2$O, 0.001% MnCl$_2$, 0.05% CaCl$_2$.2H$_2$O, 0.2% KH$_2$PO$_4$ and 0.2% (NH$_4$)$_2$SO$_4$), and cultivation with stirring and aeration was carried out at 37° C. for 20 hours (rate of aeration: 1 vvm; rate of agitation: 500 rpm). The cultured solution thus obtained was subjected to continuous centrifugation (10000 rpm, 4° C.) to remove the microbial cells and other solid matters, and the supernatant was concentrated by the use of an ultrafiltration membrane with an average molecular weight distribution of 10000 to an about ten times higher concentration. To the concentrate thus obtained, was added solid ammonium sulfate to a 30% saturation concentration, the impurities which separated out were removed by centrifugation, solid ammonium sulfate was further added to the supernatant to a 65% saturation concentration, and the resulting solution was allowed to stand overnight at 4° C. The precipitate which separated out was collected by centrifugation and dissolved in 200 ml deionized water, and this solution was dialyzed overnight against deionized water at 4° C. The solution of crude enzyme thus obtained was freeze-dried, thereby giving 3.8 g of crude enzyme powder having a pullulanase activity of 7700 unit/g.

EXAMPLE 3

The crude enzyme powder (1 g) obtained in Example 2 was dissolved in 12.5mM phosphate buffer (pH 8.0), this solution was adsorbed in an anion-exchange column (DEAE-Toyopal 650M; product of Toyo Soda Mfg. Co., Ltd.) previously equilibrated with the same buffer as above, and the enzyme was eluted by the concentration gradient method using 12.5mM phosphate buffer containing 0 to 0.5M NaCl (pH 8.0). The eluted fraction of activity was then dialyzed overnight against 25mM acetate buffer (pH 5.0) at 4° C. and adsorbed in an affinity-chromatography column charged with α-cyclodextrin-epoxy-Sephalose 6B (product of Pharmacia) previously equilibrated with 25mM acetate buffer (pH 5.0), and the enzyme was eluted by the concentration gradient method using 25mM acetate buffer (pH 5.0) containing 0 to 0.3 mg/ml β-cyclodextrin. The eluted fraction of activity was dialyzed overnight against deionized water at 4° C., and concentrated to 5.5 ml by the use of an ultrafiltration membrane with an average molecular weight distribution of 10000. The concentrate thus obtained was found to have a pullulanase activity of 150 unit/ml and to form one band when subjected to electrophoresis on sodium dedecyl sulfate.

EXAMPLE 4

The enzyme sample prepared in Example 3 was used for starch saccharification in combination with a commercially available glucoamylase. As the substrate, was used corn starch liquefied to DE12 by the use of commercially available Speedase HS (a liquefying enzyme; product of Nagase Biochemicals, Ltd.), and its concentration was set in such a level that 33 weight % of sugar will be produced. Saccharification reaction was carried out at 60° C. and pH 4.5 by using commercially available Glucoamylase XL-4 (product of Nagase Biochemicals, Ltd.) in an amount of 3.3 units per gram of the liquefied starch and the pullulanase of this invention in an amount of 4.0 units per gram of the liquefied starch. The content of dextrose in the reaction mixture was measured at different rection times by highperformance liquid chromatography. The result obtained is shown in Table 2 below.

TABLE 2

Starch saccharification by the use of the pullulanase of this invention with commercially available glucomylase

| Reaction time (hours) | % Dextrose | |
|---|---|---|
| | Control (with no pullulanase added) | With the pullulanase of this invention added |
| 17 | 90.1 | 93.2 |
| 28 | 94.8 | 96.5 |
| 40 | 94.8 | 96.3 |

EXAMPLE 5

The enzyme sample prepared in Example 3 was used for starch saccharification in combination with a commercially available β-amylase. As the substrate, was used corn starch liquefied to DE12 by the use of commercially available Speedase HS (a liquefying enzyme; product of Nagase Biochemicals, Ltd.), and its concentration was set in such a level that 33 weight % of sugar will be produced. Saccharification reaction was carried out at 60° C. and pH 4.5 by using commercially available β-amylase 1500 (product of Nagase Biochemicals, Ltd.) in an amount of 15.0 units per gram of the liquefied starch and the pullulanase of this invention in an amount of 4.0 units per gram of the liquefied starch. The content of maltose in the reaction mixture was measured at different rection times by high-performance liquid chromatography. The result obtained is shown in Table 3 below.

TABLE 3

Starch saccharification by the use of the pullulanase of this invention with commercially available β-amylase

| Reaction time (hours) | % Maltose | |
|---|---|---|
| | Control (with no pullulanase added) | With the pullanase of this invention added |
| 5 | 51.3 | 55.3 |
| 10 | 53.8 | 58.1 |
| 20 | 55.2 | 65.3 |

Compared with the α-1,6-glucosidase conventionally employed, the enzyme of this invention has a higher degree of stability under acidic conditions, and hence serves to improve sugar productivity when used in combination with glucoamylase for the manufacture of glucose from starch and when used in combination with β-amylase for the manufacture of maltose from starch.

What we claim is:

1. A process for producing a pullulanase having the physicochemical properties listed below, which comprises cultivating a microorganism belonging to the genus Bacillus and capable of producing the same in a culture medium, and collecting said pullulanase from the culture solution;
   (a) Effects and substrate specificity: activity on pullulan to form maltotriose, and cleavage of the γ-1,6-glucoside linkages in β-limit dextrin and soluble starch;
   (b) Optimum pH and pH stability: optimum pH is close to 5.0, and it remains stable in the pH range between 3.0 and 6.5 when heated at 50° C. for 30 minutes;
   (c) Thermal stability: stable at temperatures up to 55° C. when held for 30 minutes at pH 5.0;
   (d) Optimum temperature: 55° to 60° C.;
   (e) Molecular weight: 98000 as measured by electrophoresis on sodium dodecyl sulfate;
   (f) Isoelectric point: 4.7 as measured by isoelectric focusing, wherein said microorganism is *Bacillus circulans* SV-98 strain.

* * * * *